US 10,524,820 B2

(12) United States Patent
Algawi et al.

(10) Patent No.: US 10,524,820 B2
(45) Date of Patent: Jan. 7, 2020

(54) DEFLECTABLE SHAVER TOOL

(71) Applicant: Biosense Webster (Israel) Ltd., Yokneam (IL)

(72) Inventors: Yehuda Algawi, Binyamina (IL); Ilya Sitnitsky, Nahariya (IL); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 161 days.

(21) Appl. No.: 15/596,677

(22) Filed: May 16, 2017

(65) Prior Publication Data
US 2018/0333165 A1 Nov. 22, 2018

(51) Int. Cl.
*A61B 17/32* (2006.01)
*A61B 17/24* (2006.01)
*A61B 17/00* (2006.01)
*A61B 17/3207* (2006.01)
*A61B 34/30* (2016.01)

(52) U.S. Cl.
CPC ........ *A61B 17/32002* (2013.01); *A61B 17/24* (2013.01); *A61B 17/320783* (2013.01); *A61B 2017/003* (2013.01); *A61B 2017/0023* (2013.01); *A61B 2017/0046* (2013.01); *A61B 2017/00309* (2013.01); *A61B 2017/00314* (2013.01); *A61B 2017/00318* (2013.01); *A61B 2017/320024* (2013.01); *A61B 2017/320032* (2013.01); *A61B 2034/306* (2016.02); *A61B 2217/005* (2013.01)

(58) Field of Classification Search
CPC ........ A61B 17/32002; A61B 2017/003; A61B 2017/00318; A61B 2017/320032; A61B 2017/320024; A61B 2017/320028
See application file for complete search history.

(56) References Cited

U.S. PATENT DOCUMENTS

| 5,540,706 A | 7/1996 | Aust |
| 5,851,212 A * | 12/1998 | Zirps ................ A61B 17/32002 606/167 |
| 6,290,709 B1 * | 9/2001 | Ellis ................ A61B 17/32002 606/167 |
| 6,554,794 B1 | 4/2003 | Mueller |
| 6,645,218 B1 | 11/2003 | Cassidy |

(Continued)

FOREIGN PATENT DOCUMENTS

WO 2007/075989 A2 7/2007

*Primary Examiner* — Diane D Yabut
*Assistant Examiner* — Majid Jamialahmadi
(74) *Attorney, Agent, or Firm* — Volpe and Koenig, P.C.

(57) ABSTRACT

A deflectable surgical shaver tool comprises a blade with a rotatable cutting shaft comprising a distal cutting end and a proximal non-cutting end, a fixed outer sheath coaxially surrounding the rotatable cutting shaft, a cutting window at the distal cutting end, and at least a portion that is deflectable. The surgical shaver tool may further comprise an actuator; a handpiece; and a first wire and a second wire, each operatively coupled to the actuator at a proximal end and to the deflectable section at an opposite distal end. The first wire and the second wire are configured to control deflection of the deflectable portion when the actuator is manipulated. This configuration allows for the curvature of the blade to be changed for more efficient surgical procedures and prevents harm to the patient.

19 Claims, 7 Drawing Sheets

(56) References Cited

U.S. PATENT DOCUMENTS

| | | |
|---|---|---|
| 2006/0210605 A1 | 9/2006 | Chang et al. |
| 2007/0208252 A1 | 9/2007 | Makower |
| 2008/0119693 A1 | 5/2008 | Makower et al. |
| 2012/0253186 A1* | 10/2012 | Simpson ........ A61B 17/320758 600/426 |
| 2013/0023868 A1* | 1/2013 | Worrell ............ A61B 17/07207 606/33 |
| 2014/0046428 A1* | 2/2014 | Cragg ..................... A61F 2/966 623/1.12 |
| 2014/0148729 A1 | 5/2014 | Schmitz et al. |
| 2015/0066033 A1* | 3/2015 | Jorgensen .......... A61B 17/1615 606/79 |
| 2015/0335319 A1 | 11/2015 | Chin |
| 2018/0214170 A1 | 8/2018 | Algawi et al. |

* cited by examiner

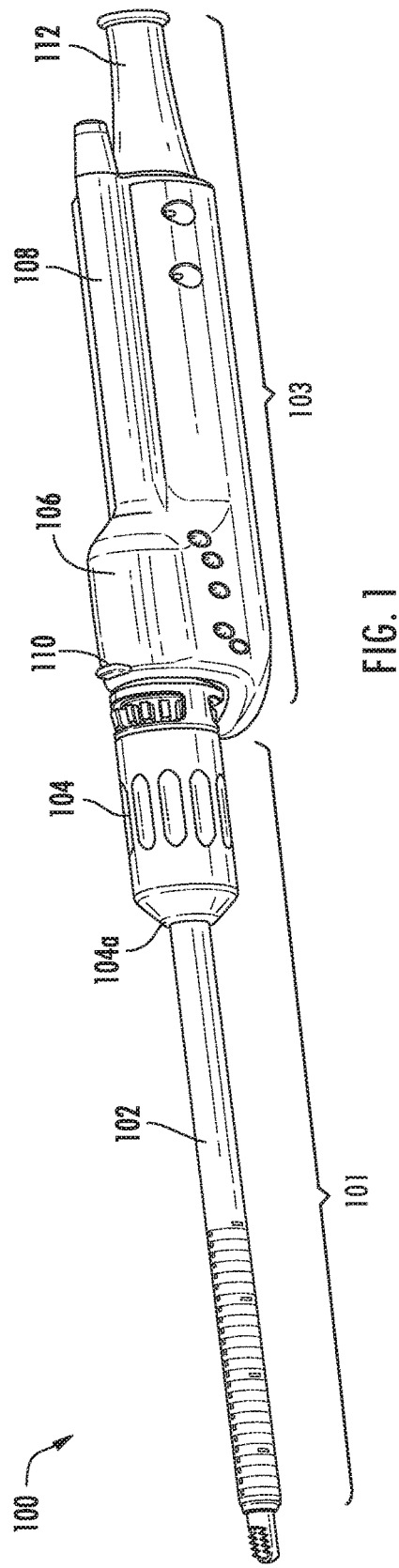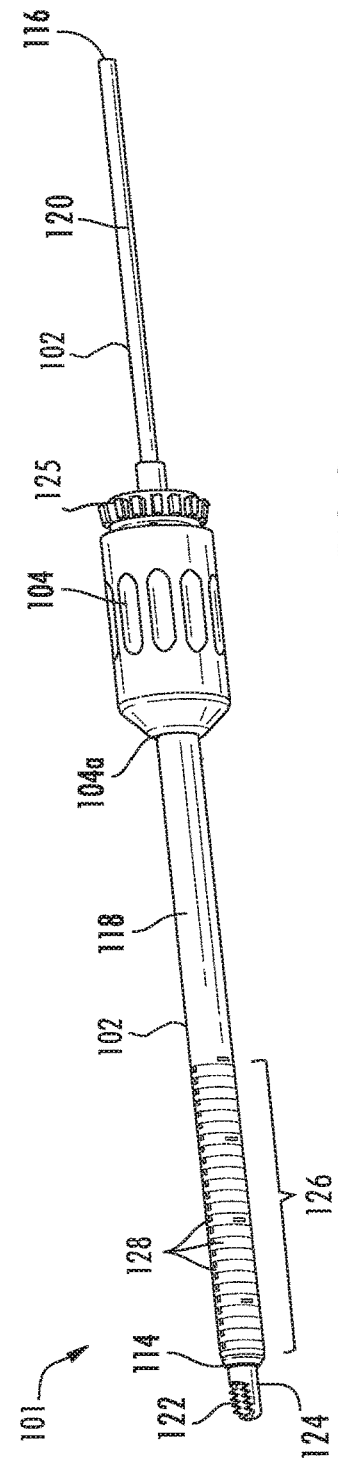

DEFLECTABLE SHAVER TOOL

SUMMARY

A surgical shaver tool comprises a blade with a rotatable cutting shaft having a distal cutting end and a proximal non-cutting end, a fixed outer sheath coaxially surrounding the rotatable cutting shaft, a cutting window at the distal cutting end, and at least a portion that is deflectable. The surgical shaver tool further comprises an actuator; a handpiece; and a first wire and a second wire, each operatively coupled to the actuator at a proximal end and to the deflectable section at an opposite distal end. The first wire and the second wire are configured to extend on opposite sides of the outer sheath, and are configured to control deflection of the deflectable portion when the actuator is rotated.

BRIEF DESCRIPTION OF THE DRAWINGS

The present invention is illustrated by way of example, and not by way of limitation, in the figures of the accompanying drawings in which:

FIG. 1 is a diagram of a perspective view of the surgical shaver tool.

FIG. 2 is a diagram of a perspective view of a disposable portion of the surgical shaver tool when the tool is in the un-deflected position.

DETAILED DESCRIPTION OF THE PREFERRED EMBODIMENTS

Figure 3A:
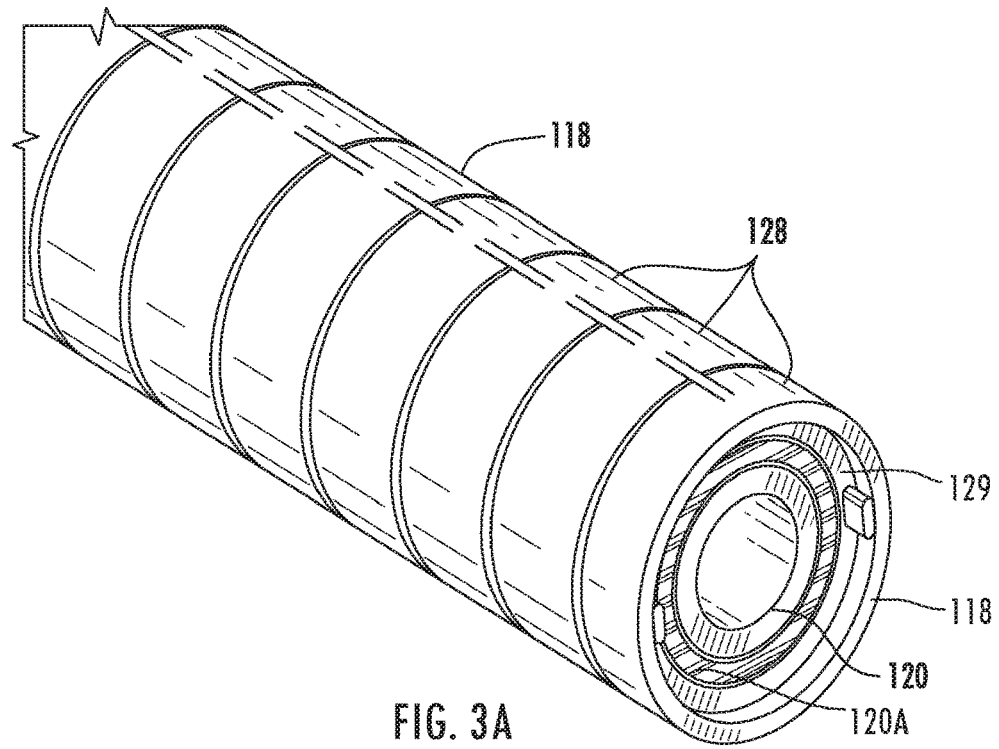
FIG. 3A is a diagram of a perspective view of a first set of interlocking ribs of an outer sheath of a blade in an un-deflected position.

ENT surgery is the surgical treatment of diseases, injuries, or deformations of the ears, nose, throat, head, and neck areas. ENT surgery encompasses a broad range of procedures and a variety of anatomical structures. The different anatomical structures present different challenges to physicians who look to provide targeted therapies to patients. As a result, numerous surgical instruments, including surgical shaver tools, must be relied upon to successfully perform such targeted procedures.

Current surgical shaver tools are designed with a non-disposable housing portion and a disposable rotatable blade. The non-disposable housing portion typically includes a handpiece, and contains a suction passage, irrigation system, and motor mechanism to drive the blade. The disposable blade comprises a shaft having a fixed curvature as well as a rotating tip and is affixed to the distal end of the non-disposable housing portion of the instrument. Utilizing this configuration, ENT physicians must use and switch between multiple shaver blades, each having a different fixed curvature corresponding to the various curved access points of the sinus cavities, in order to navigate the cavities over the course of one procedure.

It would be beneficial to offer a surgical shaver tool that permits a physician to use a single surgical tool for a precision surgical procedure, without having to switch between multiple blade curvatures during a procedure, and allows for a more efficient surgery.

FIG. 1 is a diagram of a perspective view of a surgical shaver tool 100 in accordance with the teachings herein. The surgical shaver tool 100 comprises a blade 102, an actuator 104, and a handpiece 106. In the present embodiment as described hereinafter, the surgical shaver tool 100 may include a disposable portion 101 and a non-disposable portion 103. The disposable portion 101 may include the blade 102 and the actuator 104. The actuator 104 comprises an opening 104a to allow the blade 102 to pass through the actuator 104. The blade 102 is fixed in the handpiece 106 and extends coaxially through the actuator 104 via the opening 104a. The non-disposable portion 103 may include the handpiece 106. The handpiece 106 may include a suction portion 108, a locking mechanism 110, and a power cord housing 112. The function and operation of the non-disposable portion 103 is not central to the present teachings. However, such details of the non-disposable portion 103 are set forth in U.S. application Ser. No. 15/423,214, whose disclosure is incorporated herein by reference.

In the present embodiment as described hereinafter, the surgical shaver tool 100 may be used in ENT surgeries, and for purposes of explanation, the surgical shaver tool 100 will be described with reference to ENT surgeries. However, those of skill in the art would realize that in other embodiments, the surgical shaver tool 100 may be used to perform other surgical, therapeutic, or diagnostic procedures. During ENT surgeries and procedures, a physician may insert a surgical shaver tool into a patient's sinus cavities in order to cut and remove biological material from a specific area of a cavity. Due to the varied anatomical structures within the sinus cavities, it is difficult to maneuver a single surgical instrument, such as a shaver tool, to each target surgical area. Current surgical shaver tools are rigid, and do not include a deflection system for the blade of a shaver tool. Instead, in order to navigate the surgical shaver tool to each target area, the physician must switch between multiple shaver blades with differing fixed curvatures. Having a physician switch between various curved shaver blades to navigate differing targeted sites within the sinus cavities is extremely inefficient. In addition, the patient can be harmed if the blade with the proper curvature is not selected, or if the physician tries to navigate around a cavity with a fixed curvature blade that may be difficult to maneuver. Further, since each surgical instrument typically includes a disposable portion and a non-disposable portion, using a plurality of surgical tools for a single procedure greatly increases the costs associated with the surgery both for costs for the disposable portions and sterilization costs associated with the non-disposable portions.

Returning to FIG. 1, in the present embodiment, the surgical shaver tool 100 includes a blade 102 that is deflectable when the actuator 104 is actuated. In the embodiment set forth in the drawings and as described hereinafter, the actuation is a twisting motion, but that is just by way of example. The actuation may be a sliding, pushing or electronic control. When a physician engages the actuator 104, for example by twisting the actuator 104 in one direction, the blade 102 is deflected to a particular (i.e. desired) curvature amount, to enable easier navigation inside a patient. The physician may change the curvature of the blade 102 while the blade 102 is inserted in the patient or before the blade 102 is inserted into the patient, by twisting the actuator 104. By providing a shaver tool with a selectively deflectable blade 102 that bends when a physician engages the actuator 104, surgery efficiency may increase and harm to the patient may be prevented since the blade 102 no longer needs to be removed and switched mid-procedure to navigate to the differing target sites. In addition, the costs associated with the surgery may be decreased because the cost of each disposable curvature portion and sterilization of those portions is eliminated.

FIG. 2 is a diagram of a perspective view of a disposable portion of the surgical shaver tool 100 when the tool 100 is in the un-deflected position. The disposable portion 101 may include the blade 102 and the actuator 104. The blade 102 may be a semi-rigid, hollow circular tube. The blade 102 must be rigid enough to be able to encounter and cut through biological structures and material, yet flexible enough to be navigable through the different nasal cavities. In this example embodiment, the blade 102 comprises a distal cutting end 114 located outside of the handpiece 106 (not depicted), and a proximal non-cutting end 116 located inside of the handpiece 106. The blade 102 extends from the distal cutting end 114 to the proximal non-cutting end 116.

The blade 102 includes an outer member comprising an outer sheath 118 and an inner member comprising a rotatable cutting shaft 120. The outer sheath 118 is coaxially disposed around the rotatable cutting shaft 120, thereby allowing the rotatable cutting shaft 120 to rotate freely. This configuration allows biological material to be cut or shaved when exposed to the rotating rotatable cutting shaft 120 and sucked through the rotatable cutting shaft 120 for removal from the cavity. The rotatable cutting shaft 120 must therefore be flexible and bendable in order to rotate when the blade 102 is in a deflected position, yet must be also be rigid enough to provide enough torque for the rotatable cutting shaft 120 to apply a cutting force. The rotatable cutting shaft 120 may thus comprise a hollow plastic tube to allow for flexibility during deflection. Suitable plastics include aramid fibers, polyester fibers, liquid crystal polymer fibers, such as KEVLAR, NOMEX, DACRON, SPECTRA and VECTRAN.

The outer sheath 118 must be bendable to allow for deflection, but must also be rigid enough to guide the rotatable cutting shaft 120 and apply an opposing force to the rotatable cutting shaft 120 to cut through biological material and protect the rotatable cutting shaft 120 while navigating the sinus cavities. In the present embodiment, the outer sheath 118 comprises a series of interlocking ribs 128, as depicted in FIGS. 3A-3D. The interlocking ribs 128 on the outer sheath 118 may be formed via a laser cut pattern.

FIGS. 3A-3D depict the interlocking ribs 128 formed by a laser cut pattern when the outer sheath 118 is in the un-deflected position. In the embodiment set forth in the drawings and as described hereinafter, the laser cut pattern may be various types of a "dog-bone" pattern, but this is just by way of example. In other embodiments, the laser cut pattern may be in the form of spiral cuts, window cuts, or any other suitable cut pattern or combinations of patterns to form the interlocking ribs 128, and to provide the ability for the outer sheath 118 to be bendable.

Figure 3B:
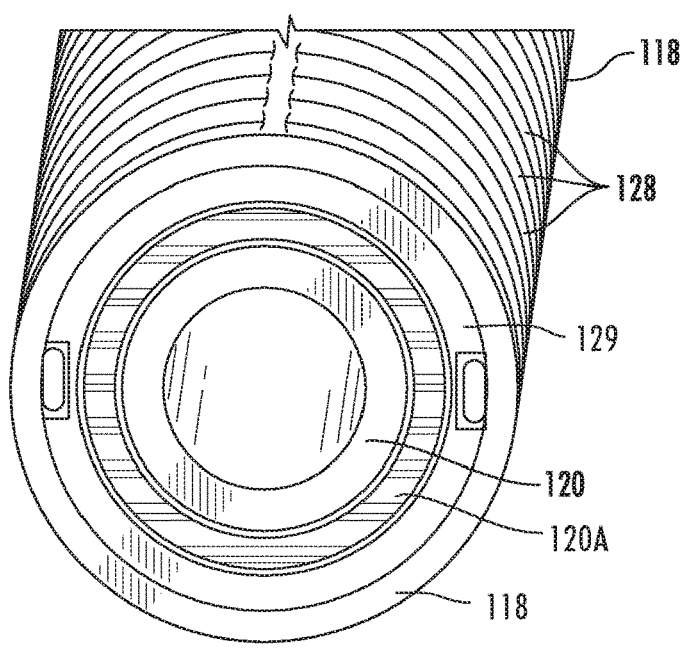
FIG. 3B is diagram of a frontal view of the first set of interlocking ribs.
Figure 3C:
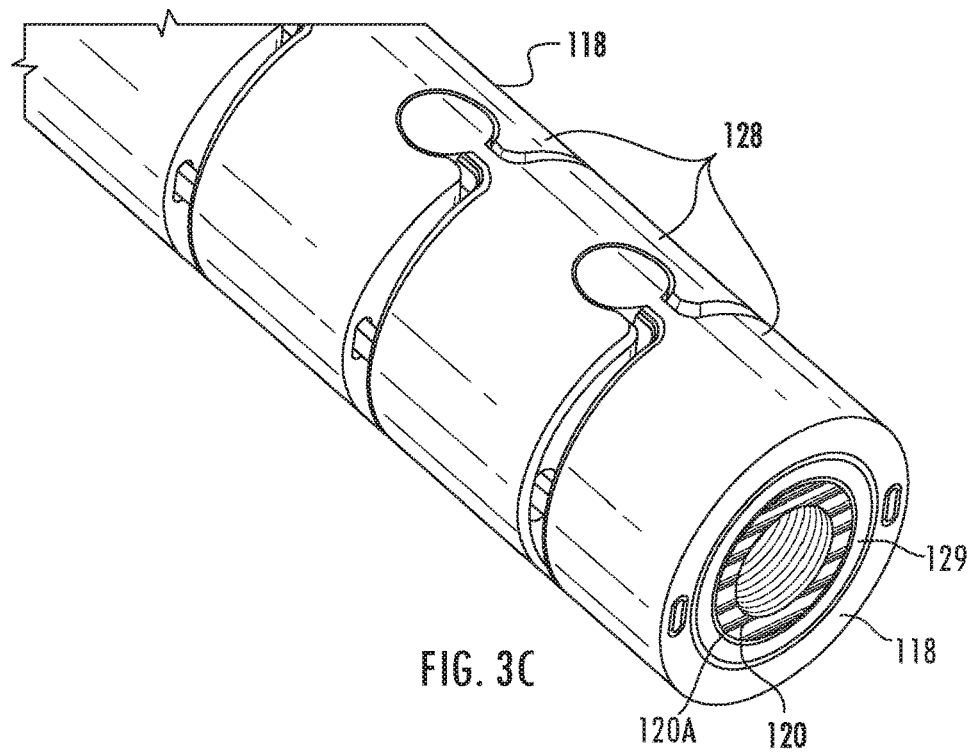
FIG. 3C is a diagram of a perspective view of a second set of interlocking ribs of an outer sheath of a blade in an un-deflected position.
Figure 3D:
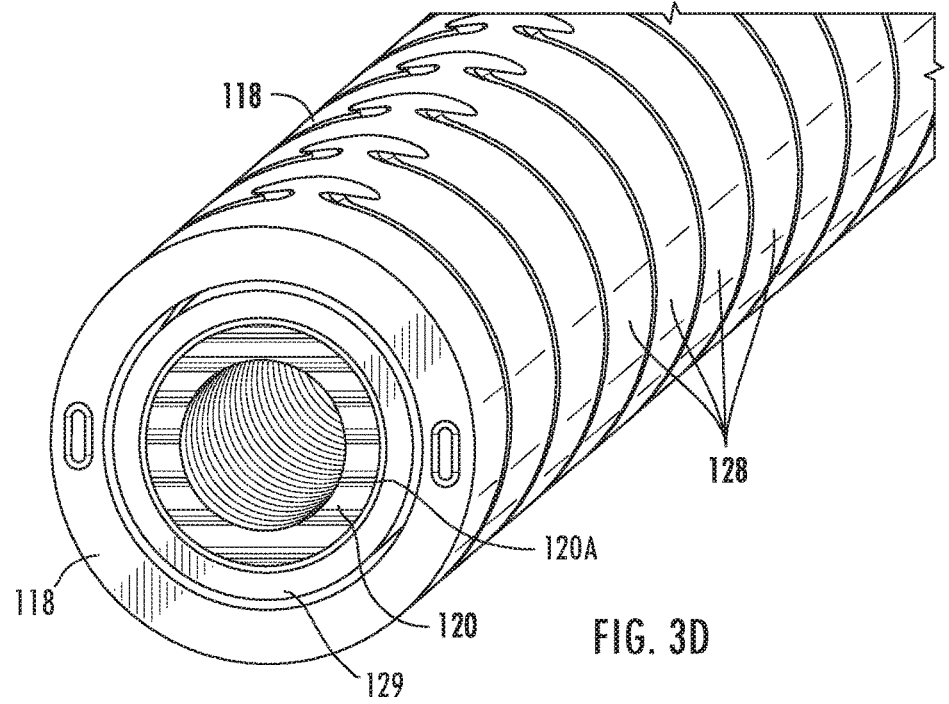
FIG. 3D is a diagram of the frontal view of the second set of interlocking ribs.

FIG. 3A is a diagram of a perspective view of a first set of interlocking ribs 128 of an outer sheath 118 of a blade 102 in an un-deflected position; while FIG. 3B is diagram of a frontal view of the first set of interlocking ribs 128. FIG. 3A and FIG. 3B depict one type of dog-bone laser cut pattern where the pattern is in the form of parallel slits between the interlocking ribs 128 that run longitudinally along the outer sheath 118. FIG. 3C is a diagram of a perspective view of a second set of interlocking ribs 128 of an outer sheath 118 of a blade 102 in an un-deflected position; while FIG. 3D is a diagram of a frontal view of the second set of interlocking ribs 128. FIG. 3C and FIG. 3D depict another type of dog-bone laser cut pattern where the pattern is in the form of a knob connected to a socket on each of the interlocking ribs 128.

The outer sheath 118 coaxially surrounds the rotatable cutting shaft 120, but does not touch the rotatable cutting shaft 120 in order to allow the rotatable cutting shaft 120 to rotate freely. In the present embodiment, the rotatable cutting shaft 120 may include a coiled or braided tube exterior 120A. The coiled or braided tube exterior 120A may increase torque transmission to the cutting tip 122 and also provide flexibility and maneuverability when the blade is rotating and deflecting. During deflection, the outer sheath 118 must be separated from the rotatable cutting shaft 120 to allow the rotatable cutting shaft 120 to rotate freely. The outer sheath 118 may thus be attached to an anchoring ring 129. In the embodiment set forth in the drawings and as described hereinafter, the anchoring is achieved via laser weld, but that is just by way of example. The anchoring ring 129 coaxially surrounds the rotatable cutting shaft 120 but does not touch the rotatable cutting shaft 120. Thus, during deflection, the anchoring ring 129 prevents the outer sheath 118 from touching the rotatable cutting shaft 120, to allow free rotation of the rotatable cutting shaft 120.

Figure 4:
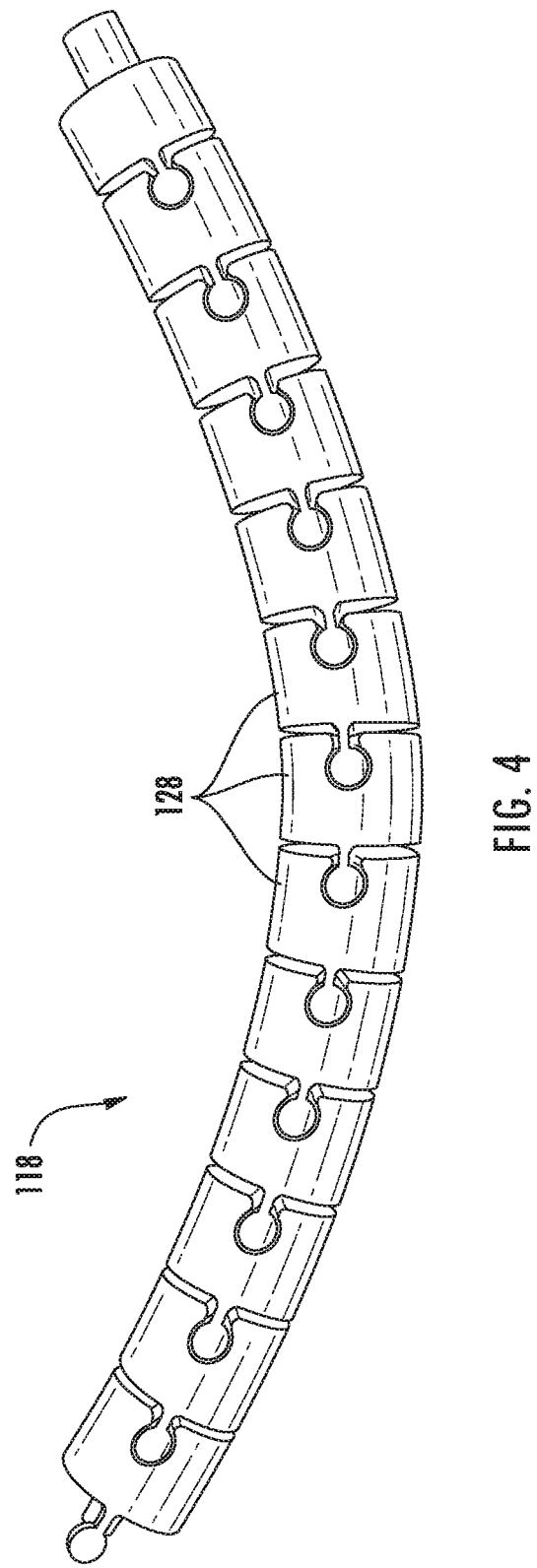
FIG. 4 is a diagram of a perspective view of a set of interlocking ribs of an outer sheath of a blade in a deflected position.

FIG. 4 is a diagram of a perspective view of a set of interlocking ribs 128 of an outer sheath 118 of a blade 102 in a deflected position. FIG. 4 depicts a laser cut pattern on the interlocking ribs 128 that is similar to the pattern of FIG. 3C and FIG. 3D. The laser cut pattern on the interlocking ribs 128 may allow for a better distribution of the strain imposed on the rotatable cutting shaft 120 and the outer sheath 118 during deflection. The cut pattern may also allow for the bendable portion 126 to deflect at greater angles.

In another embodiment, the outer sheath 118 may include a coiled tube exterior to provide bendability and offer some rigidity during deflection. The coiled exterior may be deflectable, and may allow torque to be transferred to the cutting tip 122 of the blade 102. In addition, the coiled exterior may maintain flexibility and maneuverability to navigate various cavities, and may be resistant to collapsing or buckling. In yet another embodiment, the outer sheath 118 may include a braided tube exterior. The braided tube exterior may increase torque transmission to the cutting tip 122 of the blade 102 and may also increase pushability and steerability, as well as torsional stiffness of the blade 102 in the nasal cavities. The braided exterior may also provide additional column strength, burst pressure resistance, and an increased kink radius of the outer sheath.

It should be understood by those of skill in the art that the particular material used to construct the rotatable cutting shaft 120 and outer sheath 118 of the blade 102 is not central to the invention. Rather, it is important that at least a portion of each of the rotatable cutting shaft 120 and outer sheath 118 of the blade 102 be bendable or flexible, and for the rotatable cutting shaft 120 and outer sheath 118 be able to transfer at least enough torque to enable cutting utilizing the cutting tip 122 and the cutting window 124.

Returning to FIG. 2, the rotatable cutting shaft 120 coaxially extends from the distal cutting end 114 of the blade 102, through the actuator 104, through the handpiece 106, and to the proximal non-cutting end 116. In the present embodiment, the outer sheath 118 coaxially extends from the distal cutting end 114 to a portion of the blade 102 outside of the handpiece 106. In another embodiment, the outer sheath 118 coaxially extends from the distal cutting end 114 to a portion of the blade 102 inside the handpiece 106.

In addition, the rotatable cutting shaft 120 includes a cutting tip 122 at the distal cutting end 114, and the outer sheath 118 includes a cutting window 124 at the distal cutting end 114. The rotatable cutting shaft 120 rotates such that the cutting tip 122 rotates within the cutting window 124 while the cutting window 124 remains stationary. The rotation of the cutting tip 122 while the cutting window 124 remains stationary exposes the cutting tip 122 to tissue and bone. This rotating movement debrides soft tissue and other biological material presented to the cutting window 124. The rotation of the rotatable cutting shaft 120 may be driven using any suitable mechanism, such as a direct current (DC) motor that can rotate clockwise and counterclockwise depending on the polarity of the electrical current applied to the motor.

In the present embodiment, the disposable portion 101 may include a cutter rotation knob 125. The cutter rotation knob 125 may rotate the outer sheath 118 and cutting window 124 in a clockwise and counterclockwise direction. This may be achieved by mechanically turning the cutter rotation knob 125 clockwise and counterclockwise.

Deflection occurs at a bendable portion 126 of the rotatable cutting shaft 120 and outer sheath 118 of the blade 102. The bendable portion 126 thus deflects to various curvature angles to navigate the nasal cavities. In the present embodiment, the bendable portion 126 extends from the distal cutting end 114 of the blade 102 to a portion of the blade 102 outside of the handpiece 106 (not depicted). In the present embodiment, the portion of the blade 102 that can be inserted into the nasal cavity may not be completely bendable. In another embodiment, the bendable portion 126 may include the entire portion of the blade 102 that can be inserted into the nasal cavity, and thus the portion of the blade 102 that can be inserted into the nasal cavity is completely deflectable.

Figure 5:
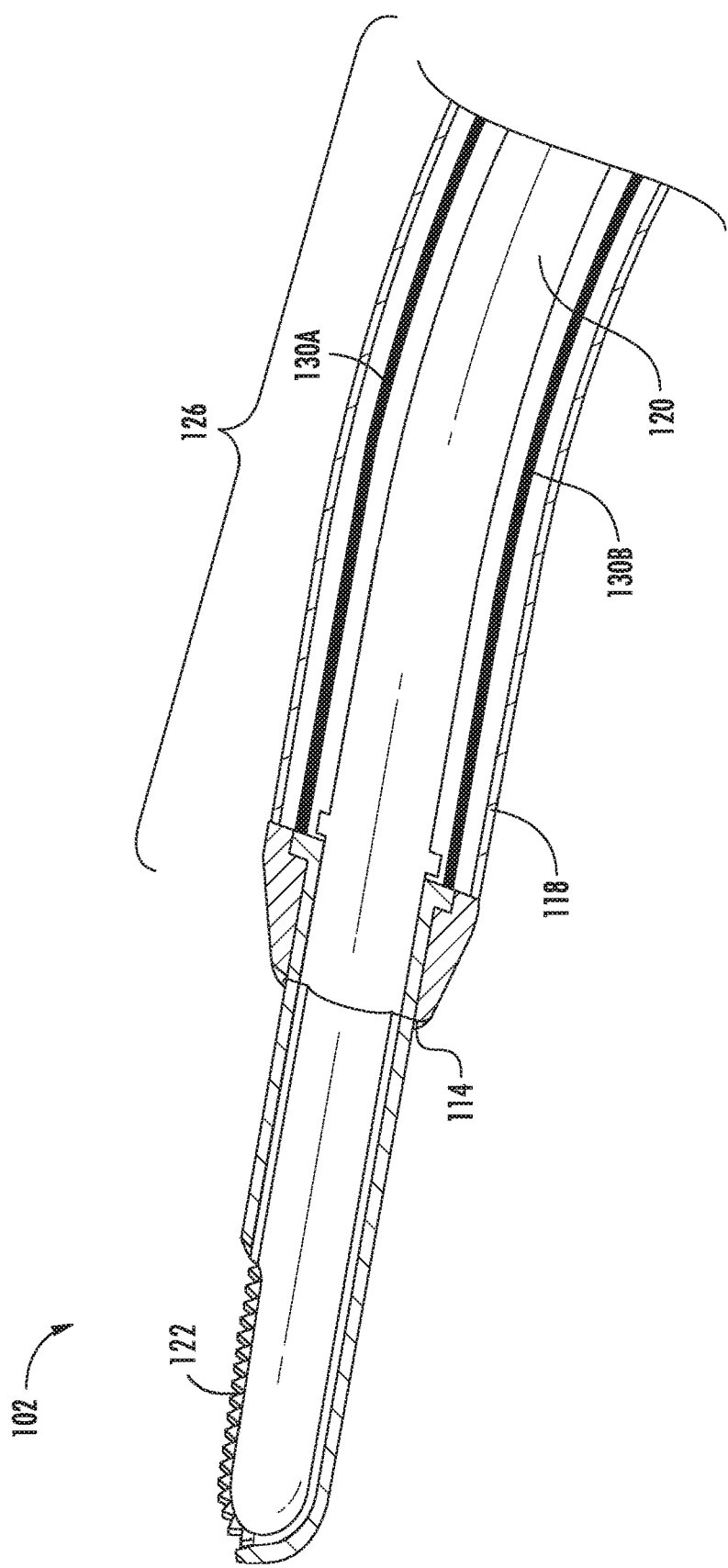
FIG. 5 is a diagram of a cross-sectional view of a portion of the blade of the surgical shaver tool in a deflected position.

FIG. 5 is a diagram of a cross-sectional view of a blade 102 of the surgical shaver tool 100 in a deflected position. When the actuator 104 (not depicted) is twisted, the bendable portion 126 of the blade 102 deflects in one direction to a particular curvature amount. The blade 102 remains in the particular deflected position until the actuator 104 is manipulated again. Deflection of the blade 102 does not affect rotation of the rotatable cutting shaft 120 to cut and remove biological material from the nasal cavities, because the configuration of the outer sheath 118 and the rotatable cutting shaft 120 allows torque to be transmitted from a gear rotating the rotatable cutting shaft 120 to the cutting tip 122. Thus, when the actuator 104 is twisted in the opposite direction, the bendable portion 126 of the blade 102 deflects in the opposite direction back towards the un-deflected position without affecting the ability of the rotatable cutting shaft 120 to rotate.

For example, a physician seeking to change the curvature of the blade 102 twists the actuator 104 (not depicted). Twisting the actuator 104 in one direction causes the bendable portion 126 of the blade 102 to increase in deflection. This may permit easier access to precise entry points inside the sinus cavities. As the physician continues to twist the actuator in the same direction, the curvature of the blade 102 increases. A greater curvature may permit the physician to access cavities that require the surgical tool to be bent at a greater angle. When the bendable portion 126 reaches the maximum deflection available, the actuator 104 is prevented from twisting any further in that same direction. If the physician wishes to decrease the curvature of the bendable portion 126 of the blade 102, the physician twists the actuator 104 in the opposite direction, until the bendable portion 126 is back to the un-deflected position.

In the present embodiment, deflection is effectuated by twisting the actuator 104 (not depicted), which manipulates two elongated wires 130A, 130B, which bend the bendable portion 126. The wires 130A, 130B are each positioned on either side of the blade 102 between the outer sheath 118 and the rotatable cutting shaft 120, and extend along the length of the blade 102 from the actuator 104 to the distal cutting end 114. Relative movement between the outer sheath 118 and the wires 130A, 130B is minimal to provide improved flexural and torsional stability along the blade 102. The wires 130A, 130B may be made of stainless steel or any other suitable material including ceramic, carbon fiber, metallic elements, alloys, plastics, or combinations thereof.

The present configuration utilizes movement of the wires 130A, 130B for more predictable deflection of the bendable portion 126 of the blade 102. For example, tensing the wire 130B and un-tensing the wire 130A pulls the bendable portion 126 of the blade 102 at the distal cutting end 114. This allows the blade 102 to curve towards the direction that the wire 130B is being pulled, (for example, downward in FIG. 5), and thereby increases deflection at the bendable portion 126. Likewise when the wire 130B is un-tensed and the wire 130A is tensed, the bendable portion 126 decreases in curvature as the wire 130A is pulled, thereby decreasing deflection at the bendable portion 126 until the blade 102 returns to an un-deflected position. Multiple curvature positions of the blade 102 may therefore be achieved based on the tensing or un-tensing of wire 130A and wire 130B.

In another embodiment, deflection of the bendable portion 126 of the blade 102 may be bi-directional. As the physician twists the actuator 104 in one direction, the curvature of the bendable portion 126 may increase in one direction. If the physician wishes to decrease the curvature back to an un-deflected position, the physician may twist the actuator 104 in the opposite direction. If the physician continues to twist the actuator 104 in the opposite direction past the un-deflected position, however, the curvature of the bendable portion 126 may increase in the opposite direction.

Figure 6:
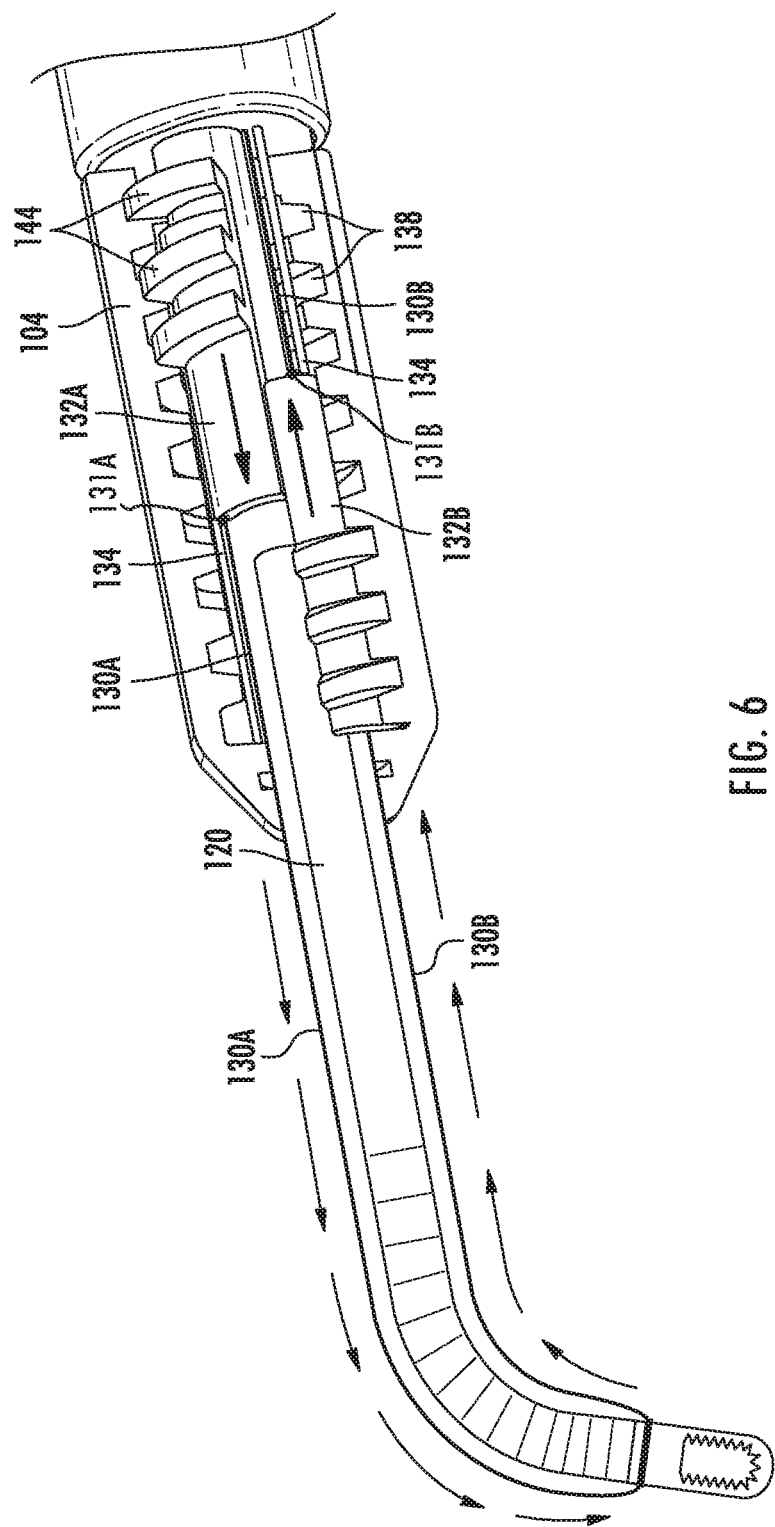
FIG. 6 is a diagram of a perspective view of the movement of wires of a surgical shaver tool when the tool is in a deflected position.

FIG. 6 is a diagram of a perspective view of the actuator 104 and the movement of wires 130A and 130B of the surgical shaver tool 100 as the tool 100 is deflected. The wires 130A, 130B are positioned generally perpendicular to the plane of the deflection of the bendable portion 126. In one embodiment, the wires 130A, 130B may be surrounded by a plastic sheath (not shown) to prevent the wires 130A, 130B from cutting into the bendable portion 126 of the outer sheath 118 when the blade 102 is deflected. In another embodiment, each wire 130A, 130B may be surrounded by a compression coil that expands longitudinally such that the surrounding compression coil is both bendable and compressible. In other embodiments, the wires 130A, 130B may be elongated bias members.

The wires 130A, 130B are anchored at a distal end to the outer sheath 118 on their respective sides near the distal cutting end 114, and are also anchored at an opposite proximal end to a set of sliders 132A, 132B, contained in the actuator 104. Slider 132A contains a spiral thread 144 spooled in one direction at its distal end, while slider 132B contains a spiral thread 144 spooled in an opposite direction at its proximal end. The inside housing of the actuator 104 also includes a thread 146 to align with the spiral thread 144 of the sliders 132A, 132B. Thus, when the actuator is twisted, the thread 146 of the actuator housing engages with the spiral thread 144 of the sliders 132A, 132B and slides the sliders 132A. The wire 130A may be anchored to the slider 132A at the distal end 131A of the slider 132A. The wire 130B may be anchored to the slider 132B at the proximal end 131B of the slider 132B. In the embodiment set forth in the drawings and as described hereinafter, the anchoring is achieved via laser weld, but that is just by way of example. The sliders 132A, 132B move in opposite directions to each other such that movement of the sliders moves the wires 130A, 130B in opposite longitudinal directions. The sliders 132A, 132B may be coupled to a guide rail 134 in the actuator 104 to allow the sliders 132A, 132B to slide in a forward and backward direction along the length of the actuator. In the present embodiment, the slider 132A partially surrounds one portion of the outer sheath 118, and the slider 132B partially surrounds the opposite portion of the outer sheath 118.

When the blade 102 is in an un-deflected position, the slider 132B is at a distal end of the actuator 104, while the slider 132A is at a proximal end of the actuator. The wires 130A and 130B are at equal tension along the length of the blade 102. When the actuator 104 is twisted in one direction to begin deflection of the blade 102, the slider 132B slides backwards along its guide rail 134 towards a proximate end of the actuator 104, as depicted by the right arrow in FIG. 6. The slider 132B pulls the wire 130B towards the proximal end of the actuator 104. As the wire 130B is pulled, tension increases in the wire 130B between the proximal end of the wire 130B where the wire 130B is anchored to the slider 132B and the distal end of the wire 130B where the wire 130B is anchored to the outer sheath 118 at the distal cutting end 114. The slider 132A simultaneously slides forward along its guide rail 134 towards a distal end of the actuator 104, as depicted by the left arrow in FIG. 6. The forward movement of slider 132A decreases the tension of the wire 130A between the proximal end of the wire 130A where the wire 130A is anchored to the slider 132A and the distal end of the wire 130A where the wire 130A is anchored to the outer sheath 118 at the distal cutting end 114. The increased tension in wire 130B and decreased tension in the wire 130A pulls the distal cutting end 114 of the blade 102 towards the proximal end of the wire 130B. The blade 102 thus deflects at the bendable portion 126 towards the proximal end of the wire 130B. When the slider 132A reaches the distal end of the actuator and the slider 132B reaches the proximal end of the actuator, the blade 102 reaches the maximum deflectable position.

The wire 130B is therefore in tension to create a bending moment to deflect the bendable portion 126 of the blade 102 to the desired curvature. As a result, the wire 130B and bendable portion 126 bends in a curvature direction towards the side of the blade that the wire 130B extends along. Thus, the plane of deflection of the bendable portion 126 of the blade 102 is perpendicular to the positioning of the wires 130A, 130B.

When the actuator 104 is twisted in the opposite direction to decrease deflection of the blade 102, the slider 132A slides backward towards the proximal end of the actuator 104. The slider 132A pulls the wire 130A backwards towards the proximate end of the actuator 104. As the slider 132A pulls the wire 130A, tension increases in the wire 130A. Simultaneously, the slider 132B slides forward towards the distal end of the actuator. The slider 132B decreases tension in the wire 130B as it moves forward toward the distal end of the actuator 104. The increased tension in wire 130A and decreased tension in the wire 130B pulls the distal cutting end 114 of the blade 102 towards the proximal end of the wire 130A. The blade 102 thus decreases deflection at the bendable portion 126 towards an un-deflected position as wire 130A and blade 102 bend in a direction toward where the wire 130A is being pulled. When the slider 132A reaches the proximal end of the actuator 104 and the slider 132B reaches the distal end of the actuator 104, the blade 102 is in the un-deflected position.

In other embodiments, the wires 130A, 130B may each be connected to spools at the proximal end. As a result, when the actuator 104 is twisted in one direction, the slider 132B slides backwards along its guide rail 134 towards a proximate end of the actuator 104, pulling and spooling the wire 130B. Simultaneously, the slider 132A slides forward along its guide rail 134 towards the distal end of the actuator 104, un-spooling the wire 130A. Thus, the tension in wire 130B is increased while the tension in wire 130A is decreased, deflecting the wires and blade 102 in the direction that wire 130B is being pulled as wire 130B is spooled.

When the actuator 104 is twisted in the opposite direction, the slider 132A slides backwards along its guide rail 134 towards a proximate end of the actuator 104, now pulling and spooling the wire 130A. Simultaneously, the slider 132B slides forward along its guide rail 134 towards the distal end of the actuator 104, un-spooling the wire 130B. Thus, the tension in wire 130A is increased while the tension in wire 130B is decreased. The deflection of the wire 130B and blade 102 is thus decreased, and the blade 102 moves towards the direction that wire 130A is being pulled as the wire 1320 is spooled.

Figure 7:
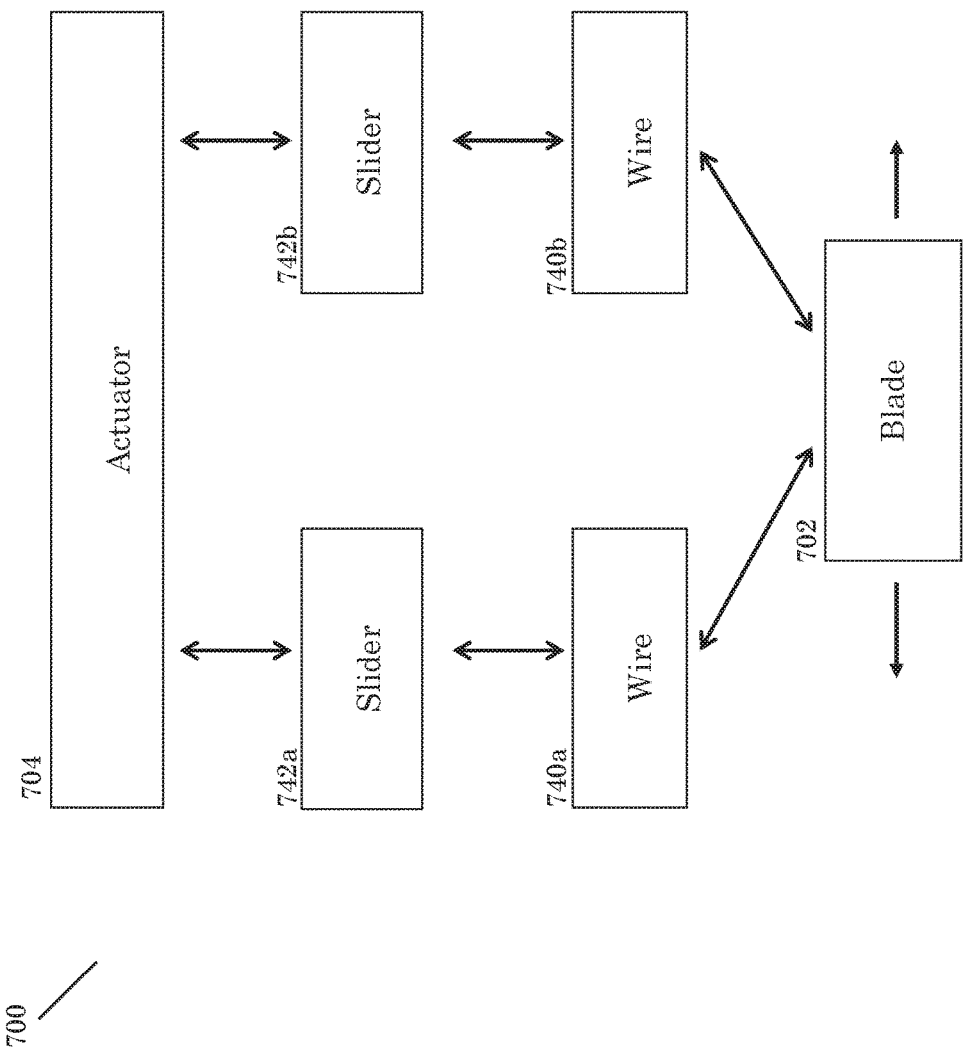
FIG. 7 is a simple block diagram of an example deflection mechanism of the surgical shaver tool.

FIG. 7 is a simple block diagram of an example deflection mechanism of the deflectable shaver tool 100. In the present embodiment, the deflection mechanism 700 comprises a blade 702, an actuator 704, wires 730A, 730B, and sliders 732A, 732B. The wire 730A is anchored to both the slider 732A and the blade 702, and the wire 730B is anchored to both the slider 732B and the blade 702. Twisting the actuator 704 controls the sliders 732A, 732B to move in opposite proximal and distal directions from each other. The movement of the sliders 732A, 732B tenses or un-tenses the wires 730A, 730B, which increases or decreases deflection based on the wire that is tensed or un-tensed.

For example, if a physician (not depicted) requires a particular blade curvature, the physician may twist the actuator 704 in one direction. The slider 732A may slide in a backwards proximal direction within the actuator 704, pulling the wire 730A in a proximal longitudinal direction and increasing the tension in the wire 730A as it is being pulled along the blade 702. The slider 732B, however, may slide in a forward distal direction, un-tensing the wire 730B in a distal longitudinal direction, decreasing tension and creating slack for the wire 730B along the blade 702. Thus, the increased tension in the wire 730A and the decreased tension in the wire 730B allow the wires 730A and 730B to bend in the direction that the wire 730A is being pulled. The blade 702 therefore bends in the same direction as the wires 730A, 730B, because the wires 730A, 730B are anchored to the blade 702.

If the physician requires a decreased curvature, the physician may twist the actuator 704 in the opposite direction. The slider 732A may slide in a forward direction within the actuator 704, un-tensing the wire 730A as it moves in a forward longitudinal direction. The slider 732B, however, may slide backward in direction, pulling the wire 730B in a backward longitudinal direction and increasing the tension in the tension in the wire 730B as it is being pulled along the blade 702. Thus, the increased tension in the wire 730B and the decreased tension in the wire 730A allow the wires 730A and 730B to bend in the direction that the wire 730B is being pulled. The blade 702 therefore bends in the same direction as the wires 730A, 730B, because the wires 730A, 730B are anchored to the blade 702.

A physician may thus change the curvature of the blade 702 while the blade 702 is inserted in the patient, or before the blade 702 is inserted into the patient, by twisting the actuator 704. Current shaver tools do not provide user-manipulated deflection of the blade. Instead, the shaver tools include multiple blades with fixed curvatures with various curved angles. A physician must navigate specific cavities of a patient using a specific blade with the desired fixed curvature angle for the specific cavity. Thus, when the physician wishes to move to another cavity during the surgery, the physician must remove the surgical shaver from the patient's body and switch the blade before inserting the shaver tool back into the patient. This maneuver prolongs the surgical procedure, and can harm the patient if the physician tries to maneuver the shaver tool with the fixed curvature around a cavity where the fixed curvature may not fit.

The present configuration allows a physician to change the curvature of the blade 702 to various desired angles without having to physically switch out the blades. Having a physician manipulate the actuator 704 to change the curvature of the blade 702 aids in navigation of the shaver tool around multiple cavities of the patient during surgery, thus increasing efficiency of the surgical procedure, preventing potential patient harm, and decreasing costs of using a shaver tool in operation.

It should be understood that many variations are possible based on the disclosure herein. Although features and elements are described above in particular combinations, each feature or element can be used alone without the other features and elements or in various combinations with or without other features and elements.

What is claimed is:

1. A surgical tool comprising:
   a blade comprising:
      a rotatable cutting shaft comprising a distal cutting end and a proximal non-cutting end, and
      an outer sheath coaxially surrounding the rotatable cutting shaft, including a cutting window at the distal cutting end, at least a portion of the outer sheath being deflectable;
   an actuator coupled to a proximal end of the outer sheath and comprising:
      a first slider surrounding a portion of the circumference of the outer sheath, and
      a second slider surrounding an opposite portion of the circumference of the outer sheath:
   a handpiece comprising a suction portion;
   a first wire operatively coupled at its proximal end to the first slider and at its distal end to the outer sheath at a distal end of the outer sheath and a second wire operatively coupled at its proximal end to the second slider and at its distal end to the outer sheath at the distal end of the outer sheath;
   wherein the first wire and the second wire deflect the deflectable portion when the actuator is manipulated; and
   wherein the outer sheath is operatively coupled to an anchoring ring at the distal cutting end and wherein the anchoring ring is located between the outer sheath and the rotatable cutting shaft.

2. The surgical tool of claim 1, wherein the rotatable cutting shaft further comprises a cutting tip operatively coupled to the rotatable cutting shaft.

3. The surgical tool of claim 1, wherein the first wire and second wire extend on opposite sides of the outer sheath.

4. The surgical tool of claim 1, wherein the anchoring ring is configured to separate the outer sheath and the rotatable cutting shaft when the blade is in both a deflected position and an un-deflected position.

5. The surgical tool of claim 1, wherein the outer sheath further comprises a braided portion.

6. The surgical tool of claim 1, wherein the outer sheath further comprises a coiled portion.

7. The surgical tools of claim 1, wherein the rotatable cutting shaft comprises a braided portion.

8. The surgical tool of claim 1, wherein the rotatable cutting shaft comprises a coiled portion.

9. The surgical tool of claim 1, wherein the outer sheath further comprises a series of interlocking ribs.

10. The surgical tool of claim 9, wherein the interlocking ribs are formed via a laser cut pattern.

11. The surgical tool of claim 1, wherein the actuator further comprises a threaded inner wall,
    the first slider comprises a threaded outer wall, and
    the second slider comprises a threaded outer wall;
    wherein the threaded inner wall engages with the threaded outer wall of the first slider and the threaded outer wall of the second slider when the actuator is manipulated.

12. The surgical tool of claim 11, wherein the engagement of the threaded outer walls and the threaded inner wall when the actuator is manipulated in one direction is configured to simultaneously slide the first slider towards a distal end of the actuator and slide the second slider towards an opposite proximal end of the actuator.

13. The surgical tool of claim 12, wherein the first and second sliders are further configured to simultaneously slide along a guide rail inside the actuator as the actuator is manipulated.

14. The surgical tool of claim 12, wherein the simultaneous sliding of the first slider and the second slider is configured to decrease tension in the first wire and increase tension in the second wire, thereby pulling the distal cutting end of the blade towards the proximal end of the second wire and increasing deflection of the blade.

15. The surgical tool of claim 11, wherein the engagement of the threaded outer walls and the threaded inner wall when the actuator is manipulated in an opposite direction is configured to simultaneously slide the first slider towards a proximal end of the actuator and slide the second slider towards an opposite distal end of the actuator.

16. The surgical tool of claim 15, wherein the simultaneous sliding of the first slider and the second slider is configured to increase tension in the first wire and decrease tension in the second wire, thereby pulling the distal cutting end of the blade away from the proximal end of the second wire and decreasing deflection in the blade.

17. The surgical tool of claim 1, wherein the blade is configured to:

cut biological material, and
pass the cut biological material from the distal cutting end to the proximal non-cutting end, and to a suction source via aspiration.

18. The apparatus of claim 1, wherein the blade is a semi-rigid hollow circular tube with constant diameter.

19. The apparatus of claim 1, wherein manipulation of the actuator is achieved by twisting the actuator in a clockwise or counterclockwise direction.

\* \* \* \* \*

UNITED STATES PATENT AND TRADEMARK OFFICE
CERTIFICATE OF CORRECTION

PATENT NO. : 10,524,820 B2
APPLICATION NO. : 15/596677
DATED : January 7, 2020
INVENTOR(S) : Yehuda Algawi et al.

It is certified that error appears in the above-identified patent and that said Letters Patent is hereby corrected as shown below:

In the Specification
In Column 1, Line 32, delete "is diagram" and insert -- is a diagram --, therefor.
In Column 3, Line 41, delete "must be also be" and insert -- must also be --, therefor.
In Column 4, Line 3, delete "is diagram" and insert -- is a diagram --, therefor.
In Column 8, Line 43, delete "730A, 730B," and insert -- 740a, 740b, --, therefor.
In Column 8, Line 44, delete "732A, 732B." and insert -- 742a, 742b. --, therefor.
In Column 8, Line 44, delete "730A" and insert -- 740a --, therefor.
In Column 8, Line 45, delete "732A" and insert -- 742a --, therefor.
In Column 8, Line 45, delete "730B" and insert -- 740b --, therefor.
In Column 8, Line 46, delete "732B" and insert -- 742b --, therefor.
In Column 8, Line 47, delete "732A, 732B" and insert -- 742a, 742b --, therefor.
In Column 8, Line 49, delete "732A, 732B" and insert -- 742a, 742b --, therefor.
In Column 8, Line 50, delete "730A, 730B," and insert -- 740a, 740b, --, therefor.
In Column 8, Line 54, delete "732A" and insert -- 742a --, therefor.
In Column 8, Line 56, delete "730A" and insert -- 740a --, therefor.
In Column 8, Line 57, delete "730A" and insert -- 740a --, therefor.
In Column 8, Line 58, delete "732B," and insert -- 742b, --, therefor.
In Column 8, Line 59, delete "730B" and insert -- 740b --, therefor.
In Column 8, Line 61, delete "730B" and insert -- 740b --, therefor.
In Column 8, Line 62, delete "730A" and insert -- 740a --, therefor.
In Column 8, Line 63, delete "730B allow the wires 730A and 730B" and insert -- 740b allow the wires 740a and 740b --, therefor.
In Column 8, Line 64, delete "730A" and insert -- 740a --, therefor.
In Column 8, Line 66, delete "730A, 730B, because the wires 730A, 730B" and insert -- 740a, 740b, because the wires 740a, 740b --, therefor.
In Column 9, Line 3, delete "732A" and insert -- 742a --, therefor.
In Column 9, Line 4, delete "730A" and insert -- 740a --, therefor.
In Column 9, Line 5, delete "732B," and insert -- 742b, --, therefor.
In Column 9, Line 6, delete "730B" and insert -- 740b --, therefor.
In Column 9, Line 8, delete "730B" and insert -- 740b --, therefor.

Signed and Sealed this
Fifteenth Day of August, 2023

Katherine Kelly Vidal
*Director of the United States Patent and Trademark Office*

CERTIFICATE OF CORRECTION (continued)
U.S. Pat. No. 10,524,820 B2

In Column 9, Line 9, delete "730B" and insert -- 740b --, therefor.
In Column 9, Lines 10-11, delete "730A allow the wires 730A and 730B" and insert -- 740a allow the wires 740a and 740b --, therefor.
In Column 9, Line 11, delete "730B" and insert -- 740b --, therefor.
In Column 9, Line 13, delete "730A, 730B, because the wires 730A, 730B" and insert -- 740a, 740b, because the wires 740a, 740b --, therefor.

In the Claims
In Column 10, Line 23, in Claim 7, delete "tools" and insert -- tool --, therefor.
In Column 11, Line 5, in Claim 18, delete "The apparatus" and insert -- The surgical tool --, therefor.
In Column 11, Line 7, in Claim 19, delete "The apparatus" and insert -- The surgical tool --.